United States Patent [19]

Imai et al.

[11] Patent Number: 5,266,497
[45] Date of Patent: Nov. 30, 1993

[54] IMMUNOCHROMATOGRAPHIC ASSAY WITH IMPROVED COLORED LATEX

[75] Inventors: Senzo Imai, Matsudo; Yoshiko Kouda, Tsuchiura; Toru Nishihara, Kainan; Masahiko Kinoshita, Sakurai, all of Japan

[73] Assignees: Japan Synthetic Rubber Co., Ltd., Tokyo; Rohto Pharmaceutical Co., Ltd., Osaka, both of Japan

[21] Appl. No.: 753,231

[22] Filed: Aug. 30, 1991

[30] Foreign Application Priority Data

Aug. 31, 1990 [JP] Japan ................. 2-228300

[51] Int. Cl.$^5$ ................ G01N 33/558; G01N 33/566; G01N 33/543; G01N 33/551; G01N 33/544; G01N 33/545; G01N 33/546; G01N 33/53; C12Q 1/00

[52] U.S. Cl. ................. 436/514; 436/501; 436/518; 436/524; 436/528; 436/531; 436/534; 436/533; 435/7.92; 435/7.93; 435/7.94; 435/7.95; 435/805; 435/970; 435/969

[58] Field of Search ............. 436/518, 524, 514, 501, 436/533, 518, 524, 514, 528, 531, 534; 435/7.92, 7.93, 7.94, 7.95, 805, 970, 969

[56] References Cited

U.S. PATENT DOCUMENTS 4,491,435 12/1983 Dorman et al. .
4,857,453 8/1989 Ullman et al. .
4,916,056 4/1990 Brown, III et al. .
5,008,080 4/1991 Brown, III et al. .

FOREIGN PATENT DOCUMENTS 227173 1/1987 European Pat. Off. .
293779 12/1988 European Pat. Off. .
299428 1/1989 European Pat. Off. .
0299428 1/1989 European Pat. Off. .

OTHER PUBLICATIONS

Brown (1987) Clin Chem 33:1567-1568.
Lim et al (1990) J Immunol Meth 135:9-14.

*Primary Examiner*—Christine M. Nucker
*Assistant Examiner*—D. R. Preston
*Attorney, Agent, or Firm*—Oblon, Spivak, McClelland, Maier & Neustadt

[57] ABSTRACT

An immunochromatography which comprises chromatographically moving a sample together with or followed by labelling fine particles in a chromatographic medium having at least one reaction site having immobilized thereat a reagent bindable to a substance to be detected in a sample, to contact the above sample and the labelling fine particles with the above reaction site, and detecting the substance to be detected by use of the phenomenon that when the above substance to be detected is present in the sample the labelling fine particles are specifically bound to the above immobilized reagent via the substance to be detected at the above reaction site, to thereby capture the substance to be detected on the chromatographic medium, characterized in that the above labelling fine particles are sensitized dyed particles obtained by sensitizing, with a material bindable to the above substance to be detected, labelling dyed particles obtained by dyeing latex particles of a synthetic high polymer, said labelling dyed particles having a surface negative charge of 0.01 to 0.5 meq/g. Said immunochromatography enables excellent visual judgement and detection of a substance to be detected which is present in a sample at a high sensitivity, and can be suitably used for the diagnosis of pregnancy.

8 Claims, No Drawings

IMMUNOCHROMATOGRAPHIC ASSAY WITH IMPROVED COLORED LATEX

BACKGROUND OF THE INVENTION
FIELD OF THE INVENTION

This invention relates to an immunochromatography using dyed latex particles of a synthetic high polymer as fine particles to which an antigen or antibody is to be bound.

As a simple immunoassay for detecting a substance to be detected which consists of a specific antigen or antibody by use of a specific reaction between antigen and antibody, there has heretofore been used an agglutination method which comprises binding, by immunoreaction, a substance to be detected, which is present in a sample, to an antibody or antigen with which fine particles have been sensitized, and then measuring the agglutination state of the fine particles thus obtained. This type agglutination method has generally been used because of its allowing visual judgement.

There has also been employed a radioimmunoassay, an enzyme immunoassay or a fluorescent immunoassay, which comprises binding, by immunoreaction, a substance to be detected, which is present in a sample, to an antibody or antigen labelled with a labelling substance consisting of a radioactive isotope, an enzyme or a fluorescent substance, respectively, and detecting the labelling substance in the bound state.

In these immunoassays, a competitive reaction or a sandwich reaction has been widely used. Immunochromatography is known as a so-called sandwich type immunoassay. In a typical immunochromatography, the following procedure is carried out in order to detect a substance to be detected consisting of an antigen in a sample:

(1) Fine particles sensitized with an antibody to an antigen, where the antigen is the substance to be detected, are immobilized as solid phase fine particles in a chromatographic medium or an antibody is immobilized directly on a chromatographic medium to thereby prepare a chromatographic medium having a reaction site or sites.

(2) Separately, fine particles are sensitized with an antibody which is specifically bindable to the substance to be detected, to thereby prepare fine particles having a labelling substance (said fine particles are referred to hereinafter as "labelling fine particles").

(3) The sensitized labelling fine particles are allowed to move chromatographically, together with a sample, in the chromatographic medium.

In the above procedure, the antibody acts as an immobilized reagent at the reaction site or sites formed in the chromatographic medium, and the sensitized labelling fine particles are specifically bound to the immobilized reagent via an antigen, which is the substance to be detected. As a result, the sensitized labelling fine particles are captured at the reaction site or sites, and the generation of a signal thereby or the intensity of the signal generated is judged by the naked eye, whereby the presence or absence and amount of the substance to be detected in the sample are determined.

In such an immunochromatography, as the fine particles used for the preparation of labelling fine particles, there have been used colloidal metal or metal oxide particles of gold, platinum, copper, iron oxide or the like; colloidal non-metal particles of sulfur or the like; and dye particles.

However, when the colloidal metal or metal oxide particles or colloidal non-metal particles are used as labelling fine particles, it is impossible to obtain labelling fine particles having a desired vivid and deep color tone because the color tone is determined by the conditions for preparing said colloidal metal or metal oxide particles or colloidal non-metal particles and the particle diameters of the colloidal metal or metal oxide particles or colloidal non-metal particles.

Meanwhile, when the dye particles are used as labelling fine particles, the color tone and depth can be selected as desired. However, their dispersion stability in water is low and difficult to control, so that the sensitization of the dye particles with an antibody is not easy. In addition, even if sensitized, the labelling fine particles obtained are difficult to resuspend and have insufficient stability. Hence, the labelling fine particles are difficult to move in an immunochromatographic medium. Moreover, even if resuspended, no uniform chromatographic movement can be achieved because the distribution of particle diameters is broad. In this respect, the dye particles are not desirable.

Thus, when the labelling fine particles consisting of colloidal metal or metal oxide particles, colloidal non-metal particles or dye particles are used, it is difficult to obtain a signal of desired intensity at the reaction site or sites of the immunochromatographic medium, or a non-uniform pattern of signal is formed. Accordingly, accurate visual judgement is difficult and it is impossible to obtain a high detection sensitivity.

SUMMARY OF THE INVENTION

This invention aims at providing an immunochromatography which can solve the above-mentioned problems, enables the intended procedure to be carried out reliably, is excellent in visual judgement and can give a high detection sensitivity.

According to this invention, there is provided an immunochromatography which comprises chromatographically moving a sample together with, or followed by, labelling fine particles in a chromatographic medium having at least one reaction site having immobilized thereat a reagent bindable to a substance to be detected in a sample, in order to contact the above sample and the labelling fine particles with the above reaction site, and detecting the substance to be detected by use of the phenomenon that when the above substance to be detected is present in the sample the labelling fine particles are specifically bound to the above immobilized reagent via the substance to be detected at the above reaction site, to thereby capture the substance to be detected on the chromatographic medium, wherein the above labelling fine particles are sensitized dyed particles obtained by sensitizing, with a material bindable to the above substance to be detected, labelling dyed particles obtained by dyeing latex particles of a synthetic high polymer, said labelling dyed particles having a surface negative charge of 0.01 to 0.5 meq/g.

DETAILED DESCRIPTION OF THE INVENTION

In the present invention, the labelling dyed particles are preferably those prepared by dyeing latex particles with an oil-soluble dye. Particularly preferably, the labelling dyed particles are those prepared by dyeing latex particles in water with an emulsion of an oil-soluble dye in an oily organic solvent.

The present invention is hereinafter described in detail referring to the case where the substance to be detected is an antigen. Needless to say, the present invention is applicable also to a case where the substance to be detected is an antibody.

The sensitized dyed particles used in the immunochromatography of the present invention are those obtained by sensitizing the labelling dyed particles (prepared by dyeing latex particles of a synthetic high polymer) with a material bindable to the substance to be detected.

The labelling dyed particles have a surface negative charge of 0.01–0.5 meq/g, preferably 0.01–0.3 meq/g, particularly preferably 0.01–0.2 meq/g. In order to produce such surface-charged labelling dyed particles, a functional group capable of imparting negative charges to the surfaces of the above-mentioned latex particles is introduced in the synthesis of latex particles. Preferable examples of such a functional group are $-COC^-$ and $-SO_4^-$. The functional group can be introduced, for example, by such a means that the latex particles are allowed to be composed of a styrene-methacrylic acid copolymer, styrene-acrylic acid copolymer or a styreneitaconic acid copolymer, or by such a means that a persulfuric acid salt or the like is used as a polymerization initiator.

Imparting negative charges to the surfaces of latex particles is also possible by adding a surface active agent to the polymerization system for synthesizing latex particles. The latex particles obtained by this approach, however, become unstable with the desorption of the surface active agent from the particle surfaces, whereby coagulation is caused in some cases. Consequently, in some cases it is impossible to carry out a preferable dyeing treatment, which is described later. Further, when the labelling dyed particles obtained from the above latex particles are sensitized with an antigen or antibody to prepare sensitized dyed particles, there is a possibility that sufficient sensitization is hindered by the surface active agent remaining on the surfaces of the labelling dyed particles and the detection sensitivity is reduced thereby.

Incidentally, the latex particles before being dyed, have a surface negative charge of ordinarily 0.01–0.5 meq/g, preferably 0.01–0.3 meq/g, particularly preferably 0.01–0.2 meq/g.

The latex particles used in the present invention have particle diameters of 0.05–0.5 μm, more preferably 0.05–0.3 μm. Latex particles having particle diameters larger than 0.5 μm are preferred in view of the fact that the signal intensity per particle of the resulting sensitized dyed particles becomes high; however, the movement of such sensitized dyed particles in the chromatographic medium is slow and difficult. Meanwhile, when latex particles having particle diameters smaller than 0.05 μm are used, there is a fear that the stability of the sensitized dyed particles becomes low.

The particle diameters of the labelling dyed particles are desirably such that the CV value (standard deviation/average) of particle diameters is 10% or less, particularly 5% or less, because such particle diameters enable uniform chromatographic movement. In the case of latex particles of a synthetic high polymer, sufficiently uniform particle diameters are obtained relatively easily. Accordingly, by using such latex particles, it is possible to obtain the preferred sensitized dyed particles.

In order to carry out a preferable dyeing treatment, there can be employed a method which comprises dissolving an oil-soluble dye having a high solubility in organic solvents, for example, an oil-soluble dye having a solubility in toluene of at least 1 g/100 ml, preferably 5 g/100 ml, in an organic solvent to prepare a dye solution, finely dispersing the dye solution in an aqueous medium in the presence of, for example, a surface active agent to prepare an oil-in-water type dye emulsion, and mixing this dye emulsion with an emulsion of latex particles to be dyed (said method is referred to hereinafter as "the dye emulsion method").

According to the dye emulsion method, labelling dyed particles having a vivid and deep tone can be obtained. Accordingly, labelling dyed particles having a more vivid tone can be obtained by repeatedly applying such a dyeing treatment for several times to the same latex particles.

By using such labeling dyed particles, the signal intensity per particle of the resulting sensitized dyed particles becomes high, and as a result, improved visual judgement can be made even by using a smaller amount of sensitized dyed particles and it becomes possible to detect a substance to be detected which is present in a sample, at a higher sensitivity. Further, the use of a smaller amount of sensitized dyed particles lowers the degree of generation of non-specific bonding and gives an increased S/N ratio; thus, an improved detection sensitivity is obtained also in this respect.

Moreover in the dye emulsion method, the surface conditions of latex particles are not varied so greatly; therefore, it is possible to reliably obtain labelling dyed particles having a surface negative charge of 0.01–0.5 meq/g.

As the oil-soluble dye used in the dye emulsion method, azo type dyes are preferred because they enable dyeing in deep color. There can also be used dyes of quinone type such as anthraquinone, naphthoquinone and the like. Specific examples of such dyes include Solvent Red 23, Solvent Red 27, Solvent Red 111, Solvent Blue 111 and their mixtures.

As another method for dyeing latex particles with an oil-soluble dye, there can be employed a method which comprises adding an organic solvent solution of an oil-soluble dye directly to an emulsion of latex particles and dyeing the latex particles by utilizing the diffusion of the oil-soluble dye.

The labelling dyed particles used in the present invention preferably have the following chroma as expressed according to Munsell's color system. That is, the dyed particles, when dried, preferably have a value L* of 40, or less, a chroma C* ($C^* = -\sqrt{a^{*2}+b^{*2}}$) of 45 or more and a hue angle H° of 240° to 60°, and more preferably have a value L* of 35 or less, a chroma C* of 55 or more and a hue angle H° of 270° (blue) to 45° (orange). It is particularly preferable that these labelling dyed particles, when measured in a dried state for reflectance for a light of 650 nm showing a red color and also for reflectance for a light of 550 nm showing an orange color by a spectrocolorimeter, give a ratio of reflectance at 650 nm/reflectance at 550 nm, of 10 or more, because such a ratio ensures visual judgement of practical utility.

The labelling dyed particles used in the present invention possess high dispersion stability in the sensitization for obtaining sensitized dyed particles, because they have a specific surface charge; accordingly, they can undergo the intended sensitization reliably without agglutination.

In order for the present invention to exhibit a higher effect, it is desirable to allow the labelling dyed particle surface to have a Zeta potential of $-20$ to $-60$ mV. By suing such labelling dyed particles, it is possible to perform an intended immunochromatographic procedure reliably, whereby excellent visual judgement is made possible and detection of a substance in a sample at a high sensitivity is also made possible.

The labelling dyed particles thus obtained are sensitized with an antibody/antigen which specifically binds to a substance to be detected which is present in a sample, whereby sensitized dyed particles are prepared. For example, when the substance to be detected is an antigen, the labelling dyed particles are sensitized with an antibody to said antigen, according to an ordinary method.

The immunochromatography of the present invention is typically carried out as follows, using the thus prepared sensitized dyed particles.

(1) A reaction site or sites are formed at an appropriate position or positions in an appropriate chromatographic medium by spotting the medium with a solution of an antibody to the antigen, which is the substance to be detected, at said position(s), or by spotting the medium with solid-phase latexes sensitized with said antibody, at said position(s), or by using other methods.

The chromatographic medium used therein is required to have an appropriate pore size larger than the particle diameter so that sensitized dyed particles can be stably and well chromatographically moved to be developed sufficiently and reliably arrive at the reaction site(s). Specific examples of the chromatographic medium are filter papers made of an inorganic fiber such as glass fiber, silica fiber or the like. The chromatographic medium can also be a filter paper made of a modified cellulose such as nitrocellulose or the like. However, a filter paper made of a cellulose per se gives an unclear signal in some cases because sensitized dyed particles are easily captured by the cellulose molecules, etc.

(2) Sensitized dyed particles are contacted with a sample and then chromatographically moved in the above-prepared chromatographic medium having reaction site(s).

Specifically, it is sufficient to mix a dispersion of sensitized dyed particles with a sample solution and allow the resulting mixture to come in contact with one end of the chromatographic medium, thereby developing the mixture sufficiently to ensure its arrival at the reaction site(s). The concentration of the sensitized dyed particles in the mixture is ordinarily 0.0001-0.05% by weight.

As a result, when the sample contains an antigen as a substance to be detected, the antigen in the sample binds to the sensitized dyed particles by specific antigen-antibody reaction and, simultaneously therewith, the antigen binds to the antibody which is the immobilized reagent at the reaction site(s) of the chromatographic medium, whereby the sensitized dyed particles are captured at the reaction site(s).

As an alternative to the above procedure (2) wherein sensitized dyed particles are contacted with a sample, it is possible to previously keep sensitized dyed particles between the reaction site of the chromatographic medium and a position in the chromatographic medium at which a sample is contacted with the chromatographic medium and freeze-dry the sensitized dyed particles. The sample is then allowed to move in the chromatographic medium by capillary action to contact the sample with the sensitized dyed particles, after which the two move together in the chromatographic medium. The sensitized dyed particles may be kept in another porous material contiguous to the chromatographic medium and freeze-dried in that state. Also in this case, when the sample contains an antigen as a substance to be detected, the sensitized dyed particles are captured as well at the reaction site(s) of the chromatographic medium.

Since the sensitized dyed particles are derived from the labelling dyed particles, the color of the labelling dyed particles appears in conformity with the shape of the reaction site(s). By visually judging the presence or absence of the color signal or its intensity, the presence, amount, etc. of the antigen which is a substance to be detected in the sample can be determined.

In the above, various embodiments are possible. For example, the number of the reaction sites formed in the chromatographic medium may be plural, and the types of the immobilized reagents present at reaction sites may be different.

It is also possible to use a chromatographic medium having not only a primary reaction site having immobilized thereat a reagent bindable to a substance to be detected but also a confirmatory reaction site having immobilized thereat a reagent not bindable to said substance but bindable to sensitized dyed particles. With this chromatographic medium, a signal appears at the primary reaction site when the sample contains a substance to be detected; meanwhile, at the confirmatory reaction site, a signal always appears regardless of whether or not the sample contains said substance; therefore, the confirmatory reaction site enables positive confirmation of the absence of the substance to be detected.

Specifically, when a mouse antibody is used to sensitize labelling dyed particles, an anti-mouse antibody obtained by inoculating the mouse antibody to a different species to give rise to immunoreaction can be used as an immobilized reagent for the formation of the confirmatory reaction site. By forming, in the chromatographic medium, the primary reaction site in the form of, for example, a vertical pattern "|" and the confirmatory reaction site in the form of, for example, a horizontal pattern "—" a signal of "+" pattern appears when the sample contains an antigen as a substance to be detected; when the sample contains no antigen, a signal of "—" pattern appears. Therefore, the pattern "+" or "—" very clearly indicates the presence or absence of the substance to be detected. The pattern "—" appearing when the substance to be detected is not present in the sample, further indicates that the sensitized dyed particles have arrived at the reaction sites and the intended immunochromatography has been carried out without fail; hence, it follows that the absence of the substance to be detected is confirmatively indicated.

In the present invention, there are used, as the labelling dyed particles, labelling dyed particles having a specific amount of surface negative charge, obtained by dyeing latex particles of a synthetic high polymer; therefore, the resulting sensitized dyed particles are well dyed and have good properties. As a result, an intended immunochromatographic procedure can be performed reliably, excellent visual judgement is possible, and accordingly a substance in a sample can be detected at a high sensitivity. The immunochromatography of the present invention can be suitably used for the diagnosis of pregnancy, in particular.

The present invention is hereinafter described with reference to Examples. However, the present invention is not restricted to these Examples.

Incidentally, the surface negative charge of latex particles or labelling dyed particles given in the following was measured by the use of Potentiograph E 536 (a product of Metler Co., Ltd.).

EXAMPLE 1

Preparation of labelling dyed particles (dye emulsion method)

A dye solution was prepared by dissolving in toluene 2.5% by weight of an oil-soluble red dye, Solvent Red 27, having a solubility in toluene of 8.5 g/100 ml at 20° C. To 1 part by weight of this dye solution was added 5.7 parts by weight of an aqueous sodium dodecyl sulfate solution having a concentration of 0.25% by weight. Dispersion was carried out by the use of an ultrasonic disperser, US 300 (a product of Kabushiki Kaisha Nihon Seiki Seisakusho) to disperse the dye solution in the aqueous solution to prepare a red dye emulsion.

Separately, a blue dye emulsion was prepared in the same manner as above, using an oil-soluble blue dye, Solvent Blue 111, having a solubility in toluene of 6.1 g/100 ml at 20° C.

42 g of the red dye emulsion was added to 100 g of an emulsion (solid content=10% by weight) of latex particles having an average particle diameter of 0.270 μm and a surface negative charge of 0.114 meq COO/g, obtained by subjecting a monomer mixture consisting of 95 parts by weight of styrene and 5 parts by weight of methacrylic acid to soap-free polymerization using potassium persulfate as a polymerization initiator. The mixture was stirred for 24 hours. Then, the mixture was subjected to steam distillation to remove the toluene. The residue was subjected to washing with distilled water by centrifugal sedimentation to remove the excess sodium dodecyl sulfate and excess dye to thereby obtain a suspension of red-dyed particle I-(1) having a surface negative charge of 0.115 meq COO/g.

The same procedure was repeated, except that the amount of the red dye emulsion was changed to 84 g or 168 g, to obtain a suspension of red-dyed particles I-(2) having a surface negative charge of 0.120 meq COO/g or a suspension of red-dyed particles I-(3) having a surface negative charge of 0.126 meq COO/g, respectively.

The same procedure as used for preparing the red-dyed particles I-(1) was repeated using 168 g of the blue dye emulsion, to obtain a suspension of blue-dyed particles I-(4) having a surface negative charge of 0.119 meq COO/g.

Each of the suspensions of dyed particles I-(1) to I-(4) was coated on a glass plate, dried and measured for light reflectance using a spectrocolorimeter, CM-1000 (a product of MINOLTA CAMERA CO., LTD.) and measured for value L*, chroma C* and hue angle using a colorimeter, CR-221 (a product of MINOLTA CAMERA CO., LTD.).

The results are shown in Table 1.

TABLE 1

| Dyed particles | I-(1) | I-(2) | I-(3) | I-(4) |
|---|---|---|---|---|
| Amount of dye emulsion added (g) | 42 | 84 | 168 | 168 |
| Amount of oil-soluble dye added per 10 g of latex particles (g) | 0.155 | 0.311 | 0.622 | 0.622 |
| Ratio of reflectances | 16[1] | 42[1] | 57[1] | 16[2] |
| Value L*[3] | 34 | 31 | 14 | 17 |
| Chroma $C^* = \sqrt{a^{*2} + b^{*2}}$ [4] | 50 | 57 | 64 | 57 |
| Hue angle H°[5] | 14 | 21 | 21 | 302 |

Note

1) Ratio of reflectances is a ratio of a reflectance for a light of 650 nm showing a red color and a reflectance for a light of 550 nm showing an orange color, i.e. reflectance at 650 nm/reflectance at 550 nm. (The same applies hereinafter.) A larger ratio of reflectances gives a color of stronger red hue.

2) Ratio of reflectances is a ratio of a reflectance for a light of 550 nm showing an orange color and a reflectance for a light of 450 nm showing a blue color, i.e. reflectance at 450 nm/reflectance at 550 nm. A larger ratio of reflectances gives a color of stronger blue hue.

3) Lightness in the CIE 1976 L*a*b* colorimetric system solid. The lager the value, the closer to white the color.

4) Vividness in the CIE 1976 L*a*b* colorimetric system chromacity diagram. The larger the value, the more vivid the color.

5) Hue angle in the CIE 1976 L*a*b* colorimetric system chromacity diagram, namely color tone.

Preparation of sensitized dyed particles

The suspension of the red-dyed particles I-(1) was diluted with a phosphate buffered saline solution (referred to hereinafter as PBS) so that the solid content after dilution became 1% by weight. 1 ml of the resulting dispersion of dyed particles and 1 ml of an antibody solution obtained by diluting a monoclonal antibody to human chorionic gonadotropin (referred to hereinafter as HCG) with PBS so that the antibody concentration after dilution became 100 μg/ml, where placed in an Eppendorf centrifugal tube and shaken at room temperature for 2 hours to sensitize the particles I-(1) with the monoclonal antibody. Thereafter, the mixture was washed three times, by centrifugal sedimentation, using PBS containing 0.1% by weight of a bovine serum albumin (referred to hereinafter as BSA), and resuspended so as to give a final volume of 2 ml, whereby a suspension of sensitized dyed particles was obtained.

The same procedure as above was repeated using the suspensions of dyed particles I-(2), I-(3) and I-(4), to obtain respective suspensions of sensitized dyed particles.

Preparation of chromatographic medium

Latex particles for solid phase were obtained by soap-free polymerization using, as monomers, 99.9 parts by weight of styrene and 0.1 part by weight of methacrylic acid and, as a polymerization initiator, potassium persulfate. The latex particles were diluted with PBS so as to give a solid content of 0.6% by weight. 1 ml of the diluted latex particles and 1 ml of a rabbit antibody solution obtained by diluting a rabbit antibody to HCG with PBS so that the antibody concentration after dilution became 100 μg/ml, were placed in an Eppendorf centrifugal tube and shaken at room temperature for 2 hours to sensitize the latex particles with the rabbit antibody. Thereafter, the mixture was washed three times, by centrifugal sedimentation, using PBS containing 0.1% by weight of BSA, and resuspended so as to give a final volume of 2 ml, whereby a solid-phase latex was prepared.

Then, a filter paper, of 100 mm in width and 80 mm in length and made of a glass fiber, was spotted with 20 μl of the solid-phase latex using an automatic TLC sampler [Linomat IV (a product of CAMAG CO., LTD.)] at a place 15-mm distant from one end. The resulting filter paper was dried in a refrigerator to prepare a chromatographic medium having a reaction site.

Preparation of HCG-containing Samples

A HCG solution, GONADOTROPIN 5000 (a product of Teikoku Hormone Manufacturing Co., Ltd.) was diluted with a PBS containing 0.1% by weight of BSA to prepare HCG-containing samples wherein the HCG concentrations were 100 mIU/ml, 50 mIU/ml and 25 mIU/ml, respectively.

Chromatographic Procedure

Each of the suspensions of sensitized dyed particles was diluted with PBS containing a 0.1% by weight of BSA and 0.001% by weight of polyoxyethylene (20) monolaurate, so as to give a solid content after dilution of 0.005% by weight. 150 μl of each of the diluted solutions of sensitized dyed particles was mixed with 150 μl of each of the HCG-containing samples, or with 150 μl of PBS containing 0.1% by weight of BSA, as a blank. Each of the resulting mixtures was stirred, after which the lower bottom portion of the above chromatographic medium which had been cut to a width of 10 mm and kept vertically was immersed in the mixture by 5 mm to develop the mixture. After 5 minutes from the start of the development, the intensity of red signal given by the sensitized dyed particles at the reaction site was visually judged.

The results of the signal intensity are shown in Table 2.

COMPARATIVE EXAMPLE 1

Preparation of gold colloidal particles 200 ml of an aqueous gold chloride solution having a concentration of 0.01% by weight was boiled. Thereto was added an aqueous sodium citrate solution having a concentration of 1% by weight. The resulting solution was boiled until the solution color turned from light yellow to purple-red, to prepare a dispension of a gold colloid having an average particle diameter of 0.03 μm.

Preparation of sensitized fine particles

To the above gold colloidal dispersion having a gold concentration of 0.01% by weight was added a potassium carbonate solution to adjust the pH of the dispersion to 7.6. Thereto was added a monoclonal antibody to HCG at a proportion of 10 μg per ml of the gold colloid dispersion. To 10 ml of the resulting mixture was added 0.1 ml of BSA solution having a concentration of 30% by weight. The mixture was subjected to centrifugal sedimentation and the resulting supernatant liquid was removed. The precipitate was washed three times by centrifugal sedimentation, using PBS containing 0.1% by weight of BSA, and resuspended to prepare gold colloidal particles A-(1) sensitized with a monoclonal antibody.

Chromatographic procedure

An immunochromatography was carried out in the same manner as in Example 1, except that the sensitized dyed particles of Example 1 were replaced by the gold colloidal particles A-(1) sensitized with a monoclonal antibody.

The results of visual judgement of the signal intensity are shown in Table 2.

TABLE 2

| Dyed particles or gold colloidal Particles | HCG concentration in sample (mIU/ml) | | | |
| --- | --- | --- | --- | --- |
|  | 100 | 50 | 25 | 0 |
| I-(1) | +++ | ++ | − | − |
| I-(2) | +++ | ++ | + | − |
| I-(3) | +++ | +++ | ++ | − |
| I-(4) | +++ | ++ | + | − |
| A-(1) | + | − | − | − |

Note

−: No color development is seen at the reaction site.

+: Color development is fairly seen at the reaction site.

++: Color development is clearly seen at the reaction site.

+++: Color development is strongly seen at the reaction site.

EXAMPLE 2

A dye solution was prepared by dissolving in toluene an oil-soluble dye, Solvent Red 111, having a solubility in toluene of 1 g/100 ml at 20° C. at a concentration of 0.21% by weight.

24 g of the dye solution was added to 100 g of the same latex emulsion as used in Example 1. The mixture was stirred for 24 hours and then subjected to steam distillation to remove the toluene. The residue was washed with distilled water by centrifugal sedimentation to obtain red-dyed particles II-(1) having a surface negative charge of 0.105 meq COO/g.

The same procedure as above was repeated, except that dye solutions containing the same dye at concentrations of 0.42% by weight and 0.84% by weight were used, to obtain a suspension of red-dyed particles II-(2) having a surface negative charge of 0.115 meq COO/g and a suspension of red-dyed particles II-(3) having a surface negative charge of 0.140 meq COO./g, respectively.

Each of the suspensions of red-dyed particles II-(1) to II-(3) was measured for light reflectance, value L*, chroma C* and hue angle in the same manner as in Example 1.

The results are shown in Table 3.

TABLE 3

| Dyed particles | II-(1) | (II-2) | II-(3) |
| --- | --- | --- | --- |
| Type of dye | Kayaset Red G | Same as left | Same as left |
| Concentration of dye solution (% by weight) | 0.21 | 0.42 | 0.84 |
| Amount of oil-soluble dye added per 10 g of latex particles (g) | 0.05 | 0.1 | 0.2 |
| Ratio of reflectances | 6 | 8 | 13 |
| Value L* | 60 | 44 | 38 |

TABLE 3-continued

| Dyed particles | II-(1) | (II-2) | II-(3) |
|---|---|---|---|
| Chroma $C^* = \sqrt{a^{*2} + b^{*2}}$ | 46 | 48 | 51 |
| Hue angle H° | 15 | 15 | 15 |

A HCG immunochromatography was carried out in the same manner as in Example 1, except that each of the suspensions of the red-dyed particles II-(1) to II-(3) was used.

The results of the visual judgement of signal intensity are shown in Table 4.

Table 4

| Dyed particles | HCG concentration in sample (mIU/ml) | | | |
|---|---|---|---|---|
| | 100 | 50 | 25 | 0 |
| II-(1) | ++ | + | − | − |
| II-(2) | ++ | + | − | − |
| II (3) | +++ | ++ | ± | − |

Note: "−", "+", "++" and "+++" have the same meanings as in Table 2 and "+" means that color development is slightly seen at the reaction site.

COMPARATIVE EXAMPLE 2

A suspension of red-dyed particles III was prepared in the same manner as for the red-dyed particles I-(3), except that there was used a latex emulsion having an average particle diameter of 0.256 μm and a surface negative charge smaller than the detection limit (0.001 meq/g), obtained by subjecting styrene (monomer) to soap-free polymerization using potassium persulfate as a polymerization initiator. However, the red-dyed particles III had a surface negative charge smaller than the detection limit; the redispersion at the time of washing by centrifugal sedimentation after sensitization was insufficient and flocs remained.

A HCG immunochromatography was carried out in the same manner as in Example 1, using the red-dyed particles III. A signal rated as + appeared even in the sample containing no HCG. Thus, the red-dyed particles III were not usable in the immunochromatography of the present invention.

What is claimed is:

1. An immunochromatography method which comprises the steps of: (a) chromatographically moving a sample together with, or followed by, labelling fine particles in a chromatographic medium having at least one reaction site having immobilized thereat a reagent bindable to a substance to be detected in a sample; (b) contacting the above sample and the labelling fine particles with the above reaction site; (c) detecting the substance to be detected by use of the phenomenon that when said substance to be detected is present in the sample the labelling fine particles are specifically bound to said immobilized reagent via the substance to be detected at said reaction site, to thereby capture the substance to be detected on the chromatographic medium, wherein said labelling fine particles are sensitized dyed particles obtained by sensitizing said labelling fine particles with a material bindable to said substance to be detected, wherein said labelling dyed particles are obtained by dyeing latex particles of a synthetic high polymer having a functional group selected from the group consisting of $-COO^-$ and $-SO_4^-$ wherein said particles have a particle diameter of 0.05-0.5 μm, the CV value (standard deviation/average) of said diameter being 10% or less, said labelling dyed particles having a surface negative charge of about 0.01 to about 0.3 meq/g, the chroma of said dyed particles as expressed according to Munsell's color system being such that when the dyed particles are dried, the value L* is 40 or less, the chroma C* ($C^* = \sqrt{a^{*2} + b^{*2}}$) is 45 more and the hue angle H° is 240° to 60°.

2. An immunochromatography method according to claim 1, wherein the surface negative charge of the labelling dyed particles is 0.01-0.2 meq/g.

3. An immunochromatography method according to claim 1, wherein the latex particles have particle diameters in the range of 0.05-0.3 μm.

4. An immunochromatography method according to claim 1, wherein the dyeing is carried out by the use of an oil-soluble dye having a solubility in toluene of at least 1 g/100 mg.

5. An immunochromatography method according to claim 1, wherein the labelling dyed particles are prepared by dyeing latex particles in water with an emulsion of an oil-soluble dye in an oily organic solvent.

6. An immunochromatography method according to claim 4, wherein the oil-soluble dye is an azo type dye or a quinone type dye.

7. An immunochromatography method according to claim 1, wherein the synthetic high polymer is a styrene-acrylic acid copolymer, a styrene-methacrylic acid copolymer or a styrene-itaconic acid copolymer.

8. The immunochromatography method according to claim 1, wherein the chromatographic medium is a filter comprises an inorganic fiber.

* * * * *